United States Patent [19]

Belloni

[11] Patent Number: 6,083,973
[45] Date of Patent: Jul. 4, 2000

[54] METHODS FOR INHIBITING MUCIN SECRETION USING RAR α SELECTIVE ANTAGONISTS

[75] Inventor: Paula Nanette Belloni, Half Moon Bay, Calif.

[73] Assignee: Syntex (U.S.A.) Inc., Palo Alto, Calif.

[21] Appl. No.: 09/256,949

[22] Filed: Feb. 24, 1999

Related U.S. Application Data

[60] Provisional application No. 60/077,328, Mar. 9, 1998.

[51] Int. Cl.$^7$ ..................................................... A61K 31/38
[52] U.S. Cl. ......................... 514/432; 514/431; 514/443; 514/569; 514/456; 514/219; 514/394; 514/339
[58] Field of Search ..................................... 514/431, 432, 514/443, 569, 456, 219, 394, 339

[56] References Cited

U.S. PATENT DOCUMENTS

| | | |
|---|---|---|
| 5,391,766 | 2/1995 | Klaus et al. |
| 5,512,683 | 4/1996 | Klaus et al. |

FOREIGN PATENT DOCUMENTS

| | | |
|---|---|---|
| WO 96/30009 | 10/1996 | WIPO . |
| WO 97/11061 | 3/1997 | WIPO . |
| WO 97/24116 | 7/1997 | WIPO . |

OTHER PUBLICATIONS

Kagechika, et al., *Biochem. and Biophy. Res. Communications*, vol. 231, pp. 243–248 (1997) "Inhibition of IL–1–Induced IL–6 Production by Synthetic Retinoids".

Apfel, et al., *Proc. Natl. Acad. Sci. USA*, vol. 89, pp. 7129–7133 (Aug. 1992) "A retinoic acid receptor antagonist selectively counteracts retinoic acid effects".

Teng, et al., *J. Med. Chem.*, vol. 40, pp. 2445–2451 (1997) "Identification of Highly Potent Retinoic Acid Receptor –Selective Antagonists".

Keidell, et al., *The Journal of Biogical Chemistry*, vol. 272:29, pp. 18267–18272 (1997) "Mutational Analysis Reveals That All–trans–retinoic, 9–cis–Retinoic acid, and Antagonist Interact with Distinct Binding Determinants of RAR ".

Frank Chytil, *American Journal Physiol*.vol. 262 (Lung Cell. Mol. Physio. 6): pp. L517–527 (1992) "The lungs and vitamin A".

Wu, et al., *Eur. Respir. Journal*, vol. 10: pp. 2398–2403 (1997) "Growth and differentiation of conducting airway epithelial cells in culture".

Eyrolles, et al.,*Journal Med. Chem.*, vol. 37: pp. 1508–1517 (1994) "Retinobenzoic Acids. 6. Retinoid Antagonists with a Heterocyclic Ring".

Guzman, et al., *Am. Journal Physiol.*, vol. 271 (Lung Cell. Mol. Physio. 15): pp. L1023–1028 (1996) "Quantitation of mucin RNA by PCR reveals induction of both MUC2 and MUC5AC mRNA levels by retinoids".

Christensen, et al.,*Am. J. Respir. Cell Mol. Biol.*, vol. 9: pp. 287–294 (1993) "Quantitative Ultrastructural Analysis of the Relationship between Cell Growth, Shape Change, and Mucosecretory Diffetiation in Cultered Hamster Tracheal Epithelial Cells Exposed to Retinoic Acid".

An, et al., *Am. J. Respir. Cell Mol. Biol.*, vol. 10: pp. 546–551 (1994) "Expression of MUC2 Gene Is Down–regulated by Vitamin A at the Transcriptional Level In Vitro in Tracheobronchial Epithelial Cells".

Steiger, et al., *Am. J. Respir. Cell Mol. Biol.*, vol. 12: pp. 307–314 (1995) "Concurrent Increases in the Storage and Release of Mucin–like Molecules by Rat Airway Epithelial Cells in Response to Bacterial Endotoxin".

Gray, et al., *Am. J. Respir. Cell Mol. Biol.*, vol. 14: pp. 104–112 (1996) "Mucociliary Differentiation of Serially Passaged Normal Human Tracheobronchial Epithelial Cells".

Eckhardt, et al., *Toxlet*, vol. 70: pp. 299–308 (1994) "A retinoic acid receptor antagonist counteracts retinoid teratogenicity in vitro and reduced incidence and/or severity of malformations in vivo".

*Primary Examiner*—James H. Reamer
*Attorney, Agent, or Firm*—Rohan Peries

[57] ABSTRACT

This invention provides methods of of inhibiting mucin production in a mammal comprising administering to the mammal an RAR antagonist. Preferably, the RAR antagonist is an RARα selective antagonist.

In another aspect, this invention provides methods of inhibiting mucin gene expression in a human epithelial cell by contacting the cell with an RAR antagonist, preferably an RARα selective antagonist.

22 Claims, 6 Drawing Sheets

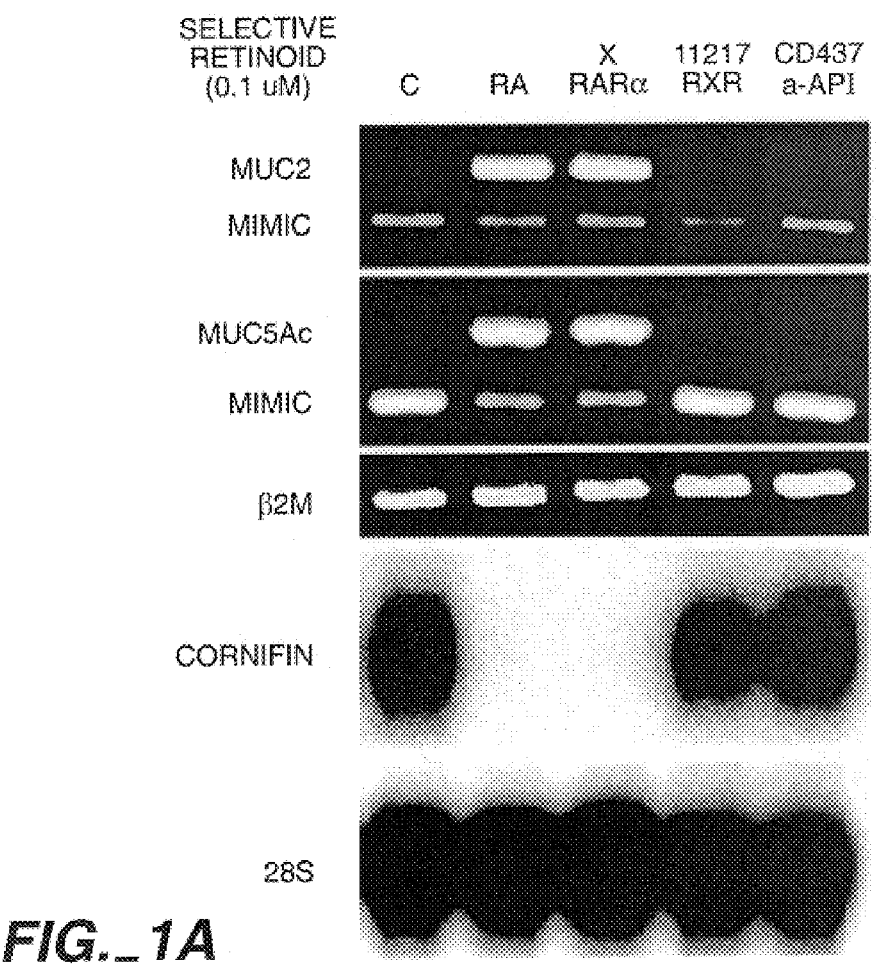
FIG._1A
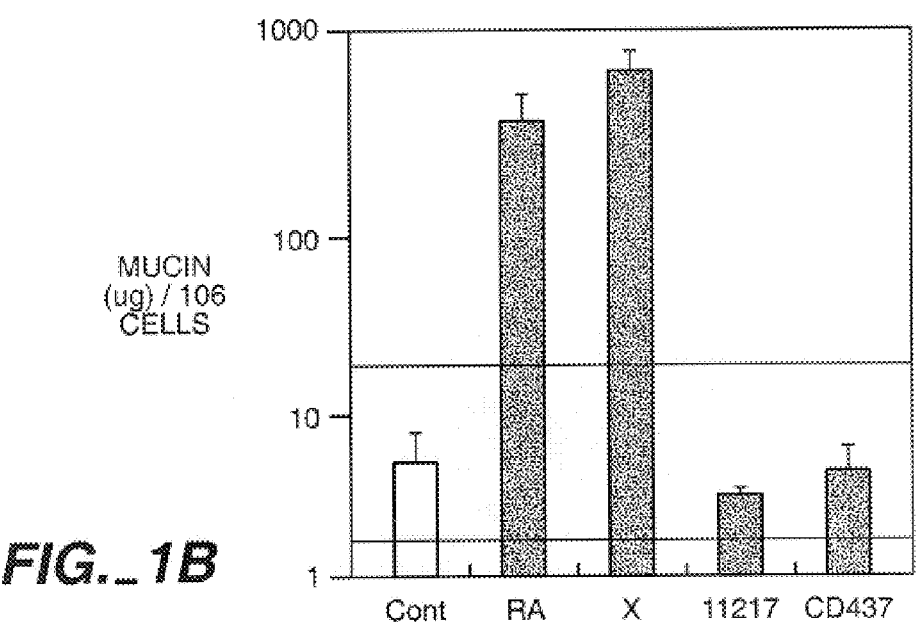
FIG._1B

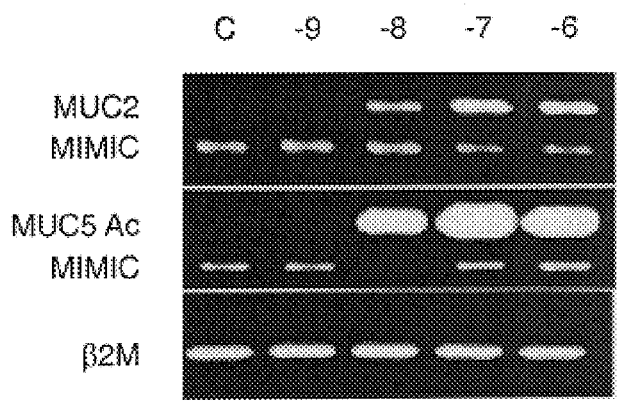
FIG._2A
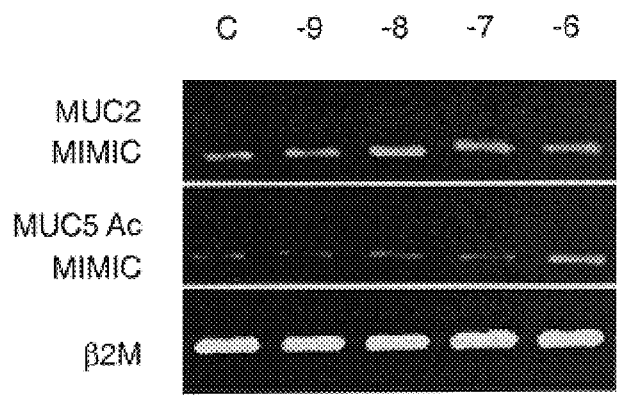
FIG._2B
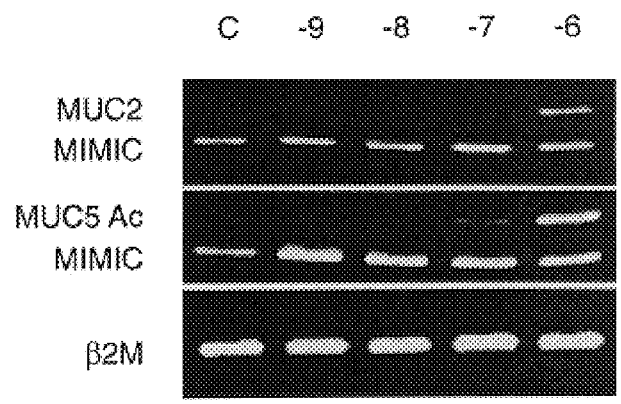
FIG._2C

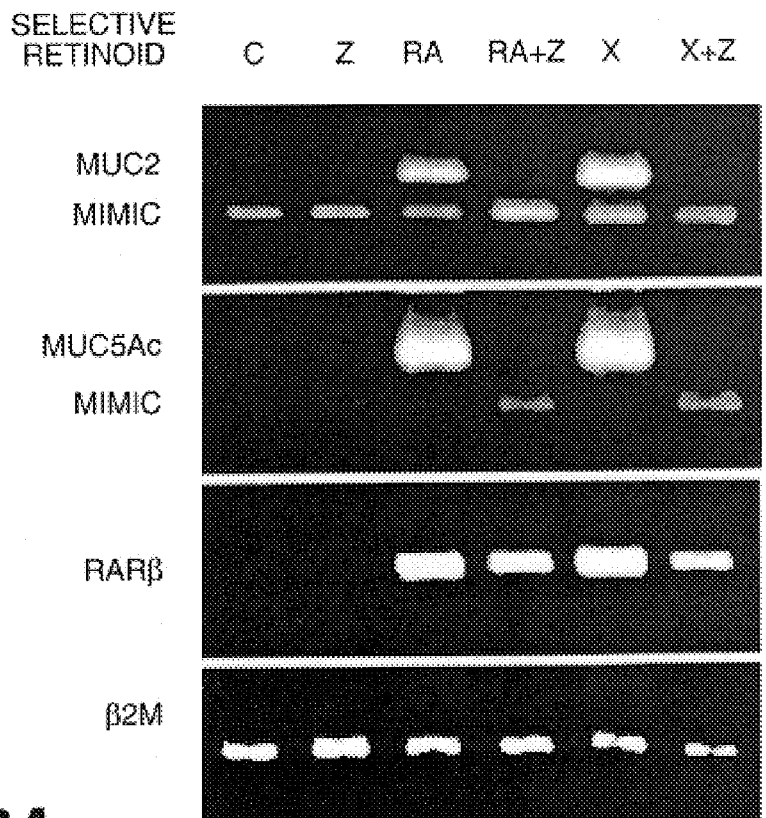
FIG._3A
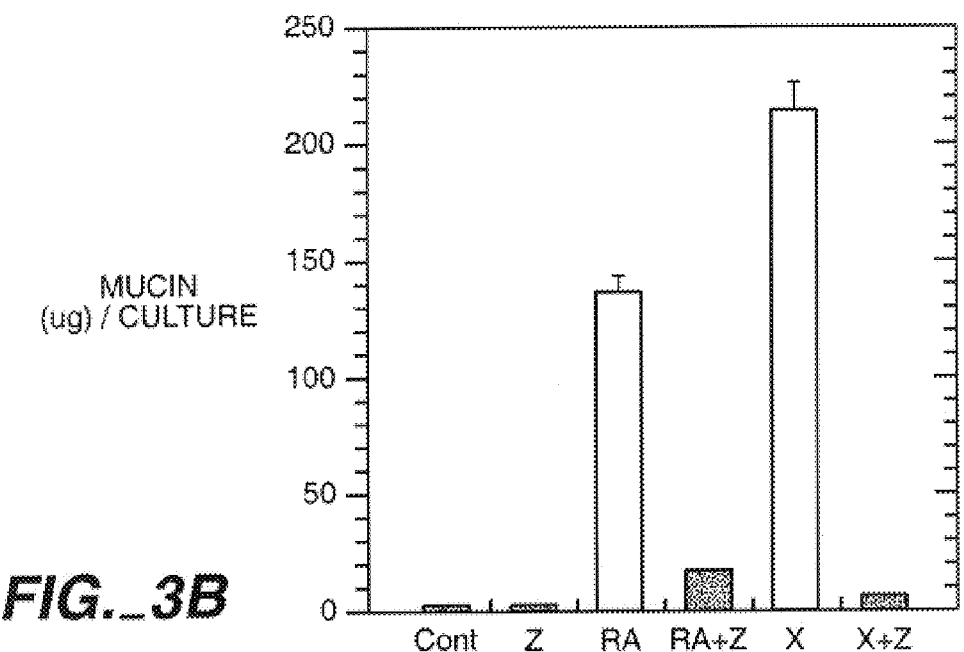
FIG._3B

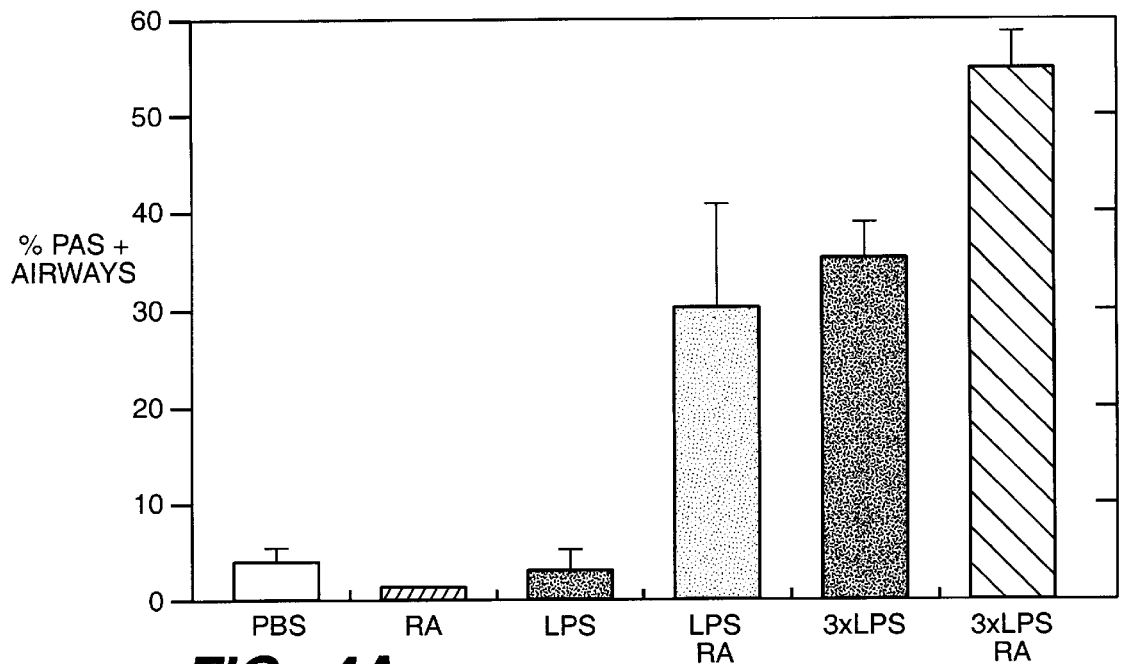
FIG._4A
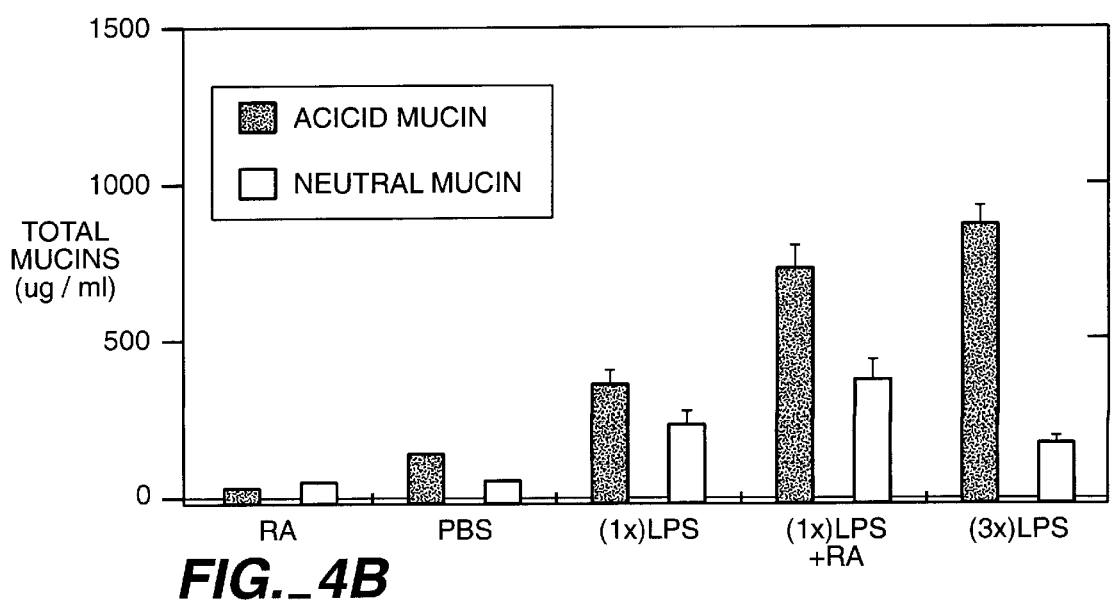
FIG._4B

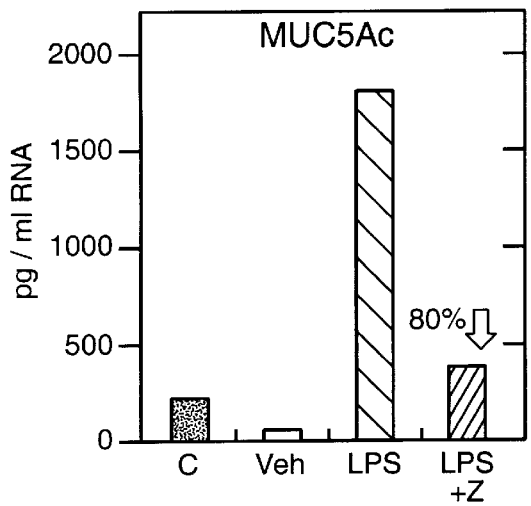
FIG._5A
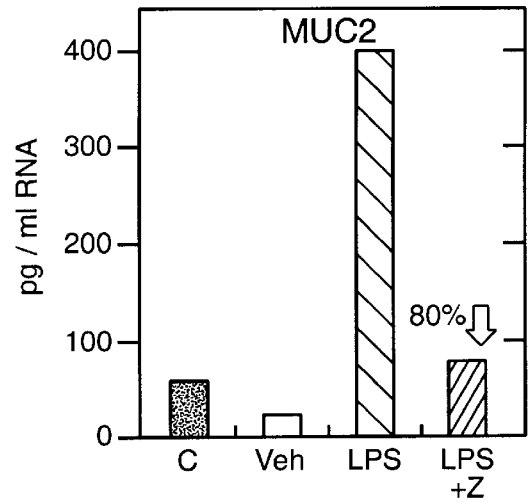
FIG._5B
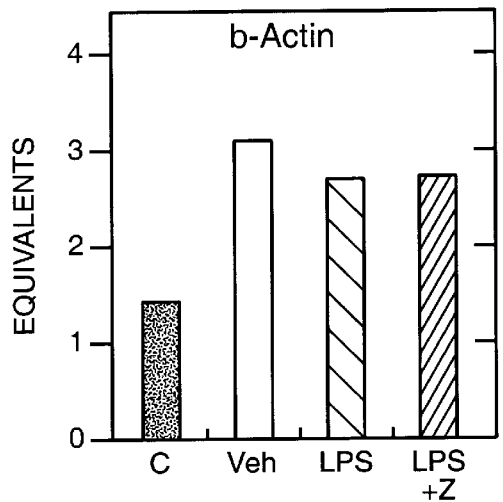
FIG._5C
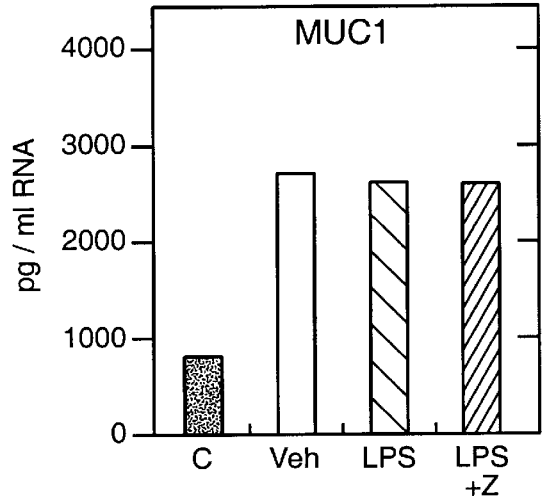
FIG._5D

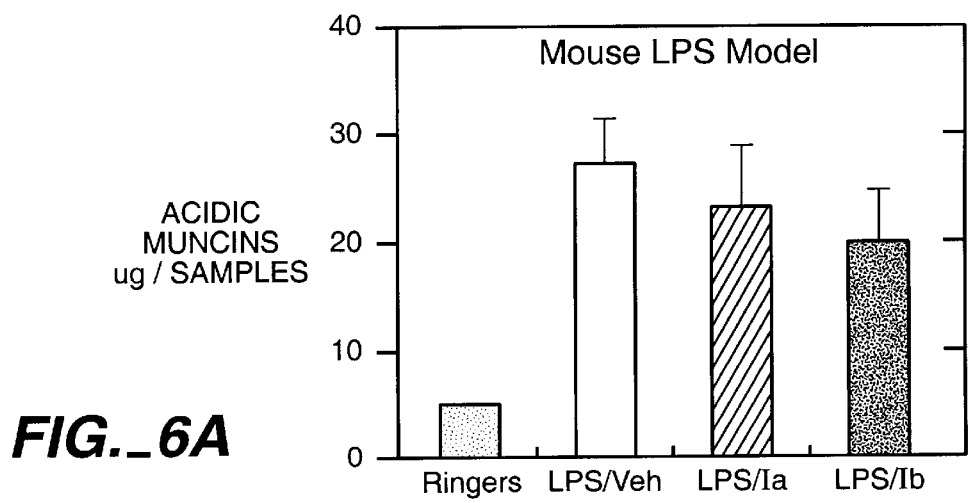
FIG._6A
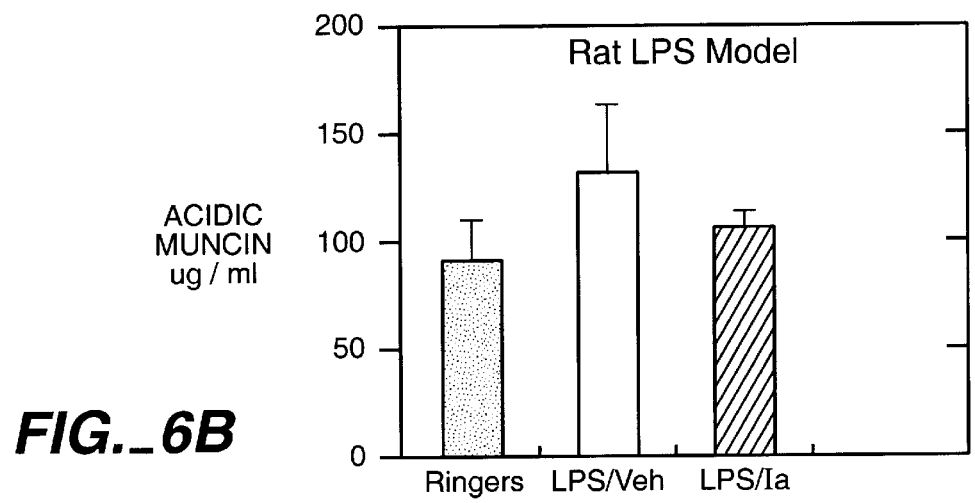
FIG._6B
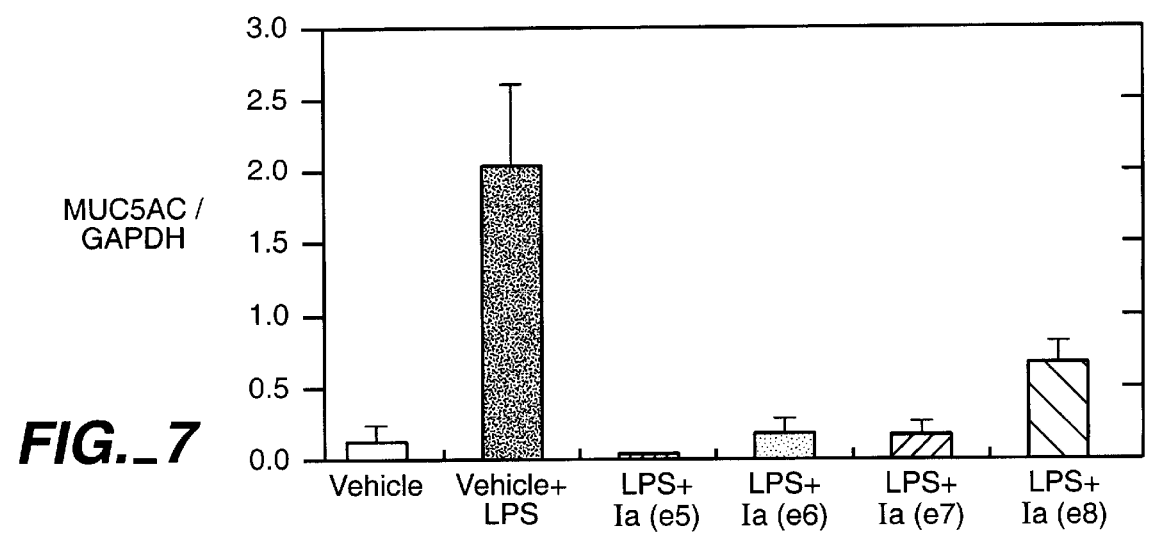
FIG._7

METHODS FOR INHIBITING MUCIN SECRETION USING RAR α SELECTIVE ANTAGONISTS

CROSS-REFERENCE TO RELATED APPLICATION

This application claims the benefit under 35 U.S.C. 119(e) of U.S. Provisional Application Ser. No. 60/077,328, filed Mar. 9, 1998, hereby incorporated by reference in its entirety.

BACKGROUND OF THE INVENTION

1. Field of the Invention

This invention relates to methods of inhibiting mucin production using retinoid acid receptor antagonists, particularly retinoid acid receptor α (RARα) selective antagonists.

2. Background Information

A. Retinoids

Retinoids are a class of compounds structurally related to vitamin A, comprising natural and synthetic compounds. A series of retinoids have been found clinically useful in the treatment of dermatological and oncological diseases. Retinoic acid and its retinoid analogs (9-cis RA, all-trans 3-4 didehydro RA, 4-oxo RA and retinol) are pleiotrophic regulatory compounds that modulate the structure and function of a wide variety of inflammatory, immune and structural cells. They are important regulators of epithelial cell proliferation, differentiation and morphogenesis in lung. Retinoids exert their biological effects through a series of nuclear receptors which are ligand inducible transcription factors belonging to the steroid/thyroid receptor superfamily. The retinoid receptors are classified into two families, the retinoic acid receptors (RARs) and the retinoid X receptors (RXRs), each consisting of three distinct subtypes (α, β, and γ). Each subtype of the RAR gene family encodes a variable number of isoforms arising from differential splicing of two primary RNA transcripts. All-trans retinoic acid (ATRA or RA) is the physiological hormone for the RAR's and binds with approximately equal affinity to all the three RAR subtypes. The RXR receptors do not bind to all-trans retinoic acid, but bind instead to the 9-cis isomer of retinoic acid.

Retinoids with retinoid receptor antagonistic activity (retinoid antagonists) are effective in counteracting many properties of retinoids with retinoid receptor agonist activity (retinoid agonists) such as inhibition of cell proliferation, induction of cell differentiation and inhibition of angiogenesis, Bollag, et al, *Int. J. Cancer*, 70:470–472 (1997) and in suppressing the toxic effects of retinoid agonists, Standeven, et al. *Toxicol. Appl. Pharmacol.*, 138:169–175 (1996). Several classes of RAR antagonists have been reported in the literature including the RARα selective antagonists described in M. Teng, et al. *J. Med. Chem.*, 40:2445–2451 (1997); C. Apfel, et al. *Proc. Nat. Acad. Sci.* (*USA*), 89:7129–7133 (1992); L. Eyrolles, et al. *J. Med. Chem.*, 37:1508–1517 (1994); H. Kagechika, et al. *Biochem. Biopharm. Res. Commun.*, 231:243–248 (1997); and PCT publication WO 96/30009.

B. Mucin Secretion

Mucins are a family of glycoproteins secreted by the epithelial cells including those at the respiratory, gastrointestinal and female reproductive tracts. Mucins are responsible for the viscoelastic properties of mucus and at least eight mucin genes are known, D. J. Thornton, et al.,*J. Biol. Chem*, 272:9561–9566 (1997). Many airway diseases such chronic bronchitis, chronic obstructive pulmonary disease, bronchietactis, asthma, cystic fibrosis and bacterial infections are characterized by mucin overproduction, E. Prescott, et al., *Eur. Respir. J.*, 8:1333–1338 (1995); K. C. Kim, et al., *Eur. Respir. J.*, 10:1438 (1997); D. Steiger, et al. *Am. J. Respir. Cell Mol. Biol.*, 12:307–314 (1995). In particular, analysis of airway secretions has identified MUC5AC and MUC5B as the primary mucin constituents of the respiratory mucus gel. Mucociliary impairment caused by mucin hypersecretion leads to airway mucus plugging which promotes chronic infection, airflow obstruction and sometimes death. For example, chronic obstructive pulmonary disease (COPD), a disorder characterized by slowly progressive and irreversible airflow limitation is a major cause of death in developed countries. The respiratory degradation consists mainly of decreased luminal diameters due to airway wall thickening and increased mucus caused by goblet cell hyperplasia and hypersecretion. Historically, mucus hypersecretion has been treated in two ways: physical methods to increase clearance and mucolytic agents. Neither approach has yielded significant benefit to the patient or reduced mucus obstruction. Therefore, it would be desirable to have methods for reducing mucin production and treating the disorders associated with mucin hypersecretion.

The reported effects of retinoids on mucin expression are in conflict. Though certain investigators have reported that vitamin A (retinol) down-regulated expression of the MUC2 gene in tracheobronchial epithelial cells, G. An, et al., *Am. Respir. Cell Mol. Biol.*, 10:546–551 (1994), others have reported that retinoid-replete cultures of normal human tracheobronchial epithelial cells produced an order of magnitude greater expression of MUC2 and MUC5AC mRNA than retinoid-depleted cells, K. Guzman, et al., *Am. J. Physiol.* 271 (*Lung Cell Mol Physiol*.15): L1023–L1028 (1996). Retinoic acid has been shown to be necessary for mucociliary differentiation of normal human tracheobronchial epithelial cells. In the absence of retinoic acid, the epithelium became squamous and mucin secretions decreased, Gray, et al., *Am. Respir. Cell Mol. Biol.*, 14:104–112 (1996). However, the mechanism by which retinoic acid mediates its effects on tracheal epithelial cells is unknown, T. G. Christensen, et al., *Am. J. Respir. Cell Mol. Biol.*, 9:287–294 (1993).

SUMMARY OF THE INVENTION

In one aspect, this invention provides methods of inhibiting mucin production in a mammal comprising administering to the mammal an RAR antagonist. Preferably, the RAR antagonist is an RARα selective antagonist with systemic administration being a preferred mode of delivery.

In another aspect, this invention provides methods of inhibiting mucin gene expression in a human epithelial cell by contacting the cell with an RAR antagonist, preferably an RARα selective antagonist.

BRIEF DESCRIPTION OF THE DRAWINGS

FIG. 1(*a*) shows induction of gene expression of MUC2 and MUC5Ac by ATRA (Retinoic Acid, indicated as RA) in human airway epithelial cells by an RARα selective agonist, Compound X.

FIG. 1(*b*) shows the increase in mucin secretion from primary human bronchial epithelium by ATRA or an RARα selective agonist, Compound X.

FIG. 2 shows the effects of RAR α, β and γ selective agonists on mucin gene expression in primary human bronchial epithelium.

FIG. 3 shows the inhibition of mucin gene expression induced by ATRA or an RARα selective agonist using an RARα selective antagonist.

FIG. 4(a) shows the enhancement in LPS induced goblet cell hyperplasia in rats by ATRA.

FIG. 4(b) shows the enhancement in LPS induced mucin hypersecretion in rats by ATRA.

FIG. 5 shows the inhibition of mucin gene expression induced by LPS using an RARα selective antagonist.

FIG. 6 shows the inhibition of mucous hypersecretion in mice and rats using RARα selective antagonists.

FIG. 7 shows a dose-response experiment for inhibition of MUC5AC mRNA transcription with an RARα selective antagonist.

DETAILED DESCRIPTION OF THE INVENTION

Definitions

As used herein, the term "$(C_{p-q})$ alkyl" means a linear or branched fully-saturated hydrocarbon radical having p to q carbon atoms; for example, a "$C_{1-4}$ alkyl" means a linear or branched fully saturated hydrocarbon radical having one to four carbon atoms, such as methyl, ethyl, propyl, isopropyl, butyl, or tertbuty. A "$(C_{p-q})$ fluoroalkyl" is an alkyl radical, as defined above, in which one or more hydrogen atoms attached to the carbon backbone have been substituted with one or more fluorine atoms.

Unless otherwise specified, the term "alkyl" means a $C_{1-4}$ alkyl radical.

As used herein, the term "$(C_{3-6})$ cycloalkyl" means a fully saturated cyclic hydrocarbon radical of three to six ring carbon atoms, e.g., cyclopropyl, cyclopentyl and the like; the term "$(C_{3-6})$ cyclofluoroalkyl" is a cycloalkyl radical, as defined above, in which one or more hydrogen atoms attached to the carbon backbone have been substituted with one or more fluorine atoms.

As used herein, the term "alkenyl" means a hydrocarbon chain of two to six carbon atoms containing at least one carbon carbon double bond (C=C), optionally methylated at one or more of the carbon atoms in the chain, and may be represented as $(C_{2-6})$ alkenyl. Representative examples include 1-propenyl, 2-pentenyl and the like. It also includes hydrocarbon chains containing a diene or a triene, such as for example 1,3-butadienyl, 1,3,5-hexatrienyl, 1,5-dimethyl-1,3,5-hexatrienyl and the like. The carbon-carbon double bonds in the alkenyl group may independently have the (E) or (Z) configuration.

As used herein, the term "alkynyl" means a hydrocarbon chain of two to six carbon atoms containing at least one carbon carbon triple bond, optionally methylated at one or more of the carbon atoms in the chain, and may be represented as $(C_{2-6})$ alkynyl. Representative examples include acetynyl, 2-propynyl, and the like. It also includes hydrocarbon chains containing a carbon-carbon double bond in addition to the carbon carbon triple bond, such as for example 2-penten-4-ynyl. These carbon-carbon double bonds may independently have the (E) or (Z) configuration.

As used herein, the term "loweralkoxy" refers to a group —OR, where R is a $(C_{1-4})$ alkyl radical.

As used herein, the term "$(C_{7-10})$ alkoxy" refers to a group OR, where R is a $(C_{7-10})$ alkyl radical.

As used herein, the term "aryl" means a monovalent monocyclic or bicyclic aromatic hydrocarbon radical of 6 to 10 ring atoms, and optionally substituted independently with one, two or three substituents selected from alkyl, haloalkyl, cycloalkyl, halo, nitro, cyano, optionally substituted phenyl, —OR (where R is hydrogen, alkyl, haloalkyl, cycloalkyl, optionally substituted phenyl), —COOR (where R is hydrogen or alkyl). More specifically the term aryl includes, but is not limited to, phenyl, 1-naphthyl, 2-naphthyl, and derivatives thereof.

"Optionally substituted phenyl" means a phenyl group which is optionally substituted independently with one, two or three substituents selected from alkyl, haloalkyl, halo, nitro, cyano, —OR (where R is hydrogen or alkyl), —NRR' (where R and R' are independently of each other hydrogen or alkyl), —COOR (where R is hydrogen or alkyl) or —CONR'R" (where R' and R" are independently selected from hydrogen or alkyl).

As used herein, the term "heteroaryl" means a monovalent monocyclic or bicyclic aromatic radical of 5 to 10 ring atoms containing one, two or three ring heteroatoms selected from N, O, or S, the remaining ring atoms being C. The aromatic radical is optionally substituted independently with one, two or three substituents selected from alkyl, haloalkyl, cycloalkyl, halo, nitro, cyano, optionally substituted phenyl, —COR (where R is alkyl, haloalkyl, or cycloalkyl), —NRR' (where R and R' are independently of each other hydrogen or alkyl), —OR (where R is hydrogen, alkyl, haloalkyl, or optionally substituted phenyl), —COOR, (where R is hydrogen or alkyl), —CONR'R", (where R' and R" are independently selected from hydrogen and alkyl). More specifically the term heteroaryl includes, but is not limited to, pyridyl, pyrimidinyl, pyrazinyl, pyridazinyl, pyrrolyl, thienyl, thiophen-2-yl, furyl, benzofuryl, indolyl, quinolyl, isoquinolinyl, benzopyranyl, pyrazolyl, thiazolyl, isothiazolyl, oxazolyl, isoxazolyl, imidazolyl, benzimidazolyl, and derivatives thereof.

As used herein, the term "retinoid" is any compound that is capable of binding to any of the α, β, or γ RAR or RXR receptors, preferably with an $IC_{50}$ of 10000 nm or less.

As used herein, the term "$EC_{50}$" of a retinoid for a retinoic acid receptor means the transactivation by the retinoid of the particular retinoic acid receptor under consideration relative to the transactivation of that same receptor by ATRA under identical conditions with both retinoids at the same concentration (1000 nM or 10000 nM depending on the highest concentration tested). Values are expressed as a percentage.

As used herein, the term "transactivation" refers to the ability of a retinoid to activate the transcription of a gene where the gene transcription is initiated by the binding of a ligand to the particular retinoic acid receptor being tested, i.e., RARα, RARβ, or RARγ. Determining the ability of a compound to transactivate a retinoic acid receptor may be performed by methods known to those of skill in the art. Examples of such methods are found in Bernard, et al. *Biochem. Biophys. Res. Commun.*, 186:977–983 (1992) and C. Apfel, et al. *Proc. Nat. Sci. Acad.* (*USA*), 89:7129–7133 (1992).

The term "$IC_{50}$" of a retinoid for a retinoic acid receptor refers to the concentration of the retinoid at which binding by ATRA to that particular receptor is inhibited by 50%. Binding is measured by competition of the retinoid with labelled ATRA.

As used herein, the term "RAR antagonist" refers to a compound which is able to bind to any of the RAR receptors and block all or part of the transactivational effects of an RAR agonist, in particular ATRA.

As used herein, the term "RARα selective antagonist" refers to a compound that is able to selectively bind to the RARα receptor and reduce RARα activation by a retinoid agonist, particularly ATRA. RARα selective antagonists will bind to the RARα receptor at significantly lower concentrations than RARβ or RARγ receptors. Selectivity is determined by comparing the $IC_{50}$'s of the retinoid for the RARα, β and γ receptors. Typically, the selectivity for the RARα receptor will be at least about 2:1, preferably at least about 10:1, more preferably at least about 100:1 and most preferably at least 1000:1 over either or both of the other RAR receptors. The lower the $IC_{50}$ of a retinoid for the RARα receptor relative to its $IC_{50}$ for the other receptors, the greater the selectivity. The antagonist effect is based on the $EC_{50}$ of the retinoid for the RARα receptor. Typically, the $EC_{50}$ of the retinoid antagonist for the RARα receptor is less than about 50, preferably less than about 30, more preferably less than 20 and most preferably less than 10. Generally, the $EC_{50}$'s of RARα selective antagonists are in the range of 2 to 50.

"Pro-drug" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include retinoid antagonists wherein a hydroxy or carboxy group in the antagonist is bonded to any group that may be cleaved in vivo to regenerate the free hydroxyl or carboxy group. Examples of prodrugs include, but are not limited to esters (e.g., acetate, formate, methyl and ethyl esters, and benzoate derivatives), carbamates (e.g., N,N-dimethylaminocarbonyl) and ethers of hydroxy or carboxy functional groups in the antagonists, and the like. Such compounds are routinely made by one of skill in the art by esterifying, acylating or etherifying the hydroxy or carboxy group in the parent molecule.

A "therapeutically effective amount" means the amount of a compound that, when administered to a mammal for treating or preventing a disease, is sufficient to effect such treatment or prevention for the disease. The "therapeutically effective amount" will vary depending on the compound, the disease and its severity and the age, weight, etc., of the mammal to be treated.

The present invention relates to the discovery that RAR antagonists, particularly RARα selective antagonists, are effective inhibiting mucin secretion.

The present inventor has observed that all trans retinoic acid (ATRA) transactivates mucin gene expression, specifically MUC2 and MUC5AC expression, in human epithelial cells Further investigation surprisingly showed that this effect of retinoic acids was mediated specifically through the RARα receptor. Whereas RARα selective retinoid agonists induced MUC2 and MUC5AC expression in human epithelial cells, neither RARβ nor RARγ selective agonists did so, even at high doses of compound. Thus, activation via RARα is necessary and sufficient for mucin expression. This effect of retinoid induced mucin gene expression was inhibited by RARα selective antagonists, in particular by (p-[(E)-2-[3'4'-Dihydro-4,4'-dimethyl-7'-(heptyloxy)-2'H-1-benzothiopyran-6'-yl]propenyl]benzoic acid 1'1'-dioxide (Compound Ia), and ((all-E)-7-[7'-(heptyloxy)-3',4'-dihydro-4,4'-dimethyl-2'H-1-benzothiopyran-6'-yl]-3-methyl-2,46-octatrienoic acid 1,1'-dioxide (Compound Ib).

As described in more detail in the Examples, RARα selective antagonists also inhibited LPS induced mucin expression, and inhibited mucin hypersecretion in the rat model of airway inflammation. On a morphological level, RARα selective antagonists were also shown to reduce differentiation of epithelial cells to goblet cells, thus reducing goblet cell induced hyperplasia.

Consequently, one aspect of this invention is the inhibition of mucin production in a mammal by administering to the mammal an RAR antagonist, preferably an RARα selective antagonist. RAR antagonists are less toxic to mammals than RAR agonists.

Selected RAR antagonists that are useful in reducing mucin secretion as described herein are generally described, in part, in U.S. Pat. Nos. 5,512,683 and 5,391,766; PCT Patent publications WO 96/30009, WO 97/24116, and WO 97/11061; S. Kaneko et al. *Med. Chem. Res.*, 1:220–225 (1991); L. Eyrolles, et al., *Med. Chem. Res.*, 2:361–367 (1991); L. Eyrolles, et al. *J. Med. Chem*, 37:1508–1517 (1994); H. Kagechika, et al., *Biochem. Biophys. Res. Commun.*, 231:243–248 (1997); C. Apfel, et al., *Proc. Natl. Acad. Sci.* (*USA*), 89:7129–7133 (1992); K. Eckhardt, et al., *Toxicol. Lett.*, 70:299–308 (1994); and M. Teng, et al., *J. Med. Chem.*, 40:2445–2451 (1997). However, it will be recognized by one of skill in the art that the present invention encompasses the use of all RAR antagonists and RARα selective antagonists and is not limited to those antagonists described above or presently known to the art. Generally, all compounds which have RAR antagonist or RARα selective antagonist activity are useful for the methods of the invention.

A particularly preferred aspect of this invention is the use of RARa selective antagonists to inhibit mucin secretion. RARα selective antagonists are those compounds that bind selectively to the RARα receptor and reduce the RARα transactivational effect of a retinoid agonist, i.e. ATRA as defined earlier.

The RARα antagonist selectivity of a compound can be determined by routine ligand binding assays known to one of skill in the art such as described in C. Apfel, et al. *Proc. Nat. Sci. Acad.* (*USA*), 89:7129–7133 (1992); M. Teng, et al, *J. Med. Chem.*, 40:2445–2451 (1997); and PCT Publication WO 96/30009.

In one aspect, RAR antagonists used in this invention have the structure of Formula I:

Formula I

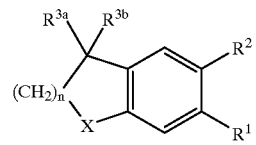

wherein

X is S, SO, or $SO_2$;

$R^1$ is $C_{7-10}$ alkyl or $C_{7-10}$ alkoxy;

$R^2$ is carboxyaryl, loweralkoxycarbonylaryl, carboxyalkenyl, lowealkoxycarbonylalkenyl, carboxyalkynyl, loweralkoxycarbonylalkynyl, carboxyarylalkenyl, loweralkoxycarbonylarylalkenyl, carboxyarylalkynyl or loweralkoxycarbonylarylalkynyl;

$R^{3a}$ and $R^{3b}$ are independently hydrogen or $C_{1-4}$ alkyl; and n is an integer from 1 to 3 inclusive.

Preferred compounds are those where $R^2$ is:

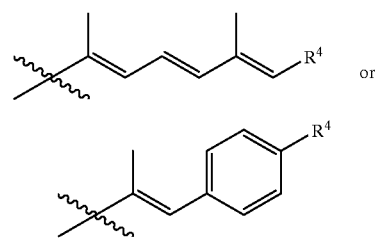

where $R^4$ is carboxyl or loweralkoxycarbonyl.

A representative selection of R antagonists within the family of compounds of Formula I and their transactivation $EC_{50}$ and RAR binding constant ($IC_{50}$) to the RARα, β and γ receptors is shown below in Table I.

| Structure | Transactivation | | RAR Binding | |
|---|---|---|---|---|
| | $EC_{50}$ | % MAX | | $IC_{50}$ |
| (structure 1: thiochromane S,S-dioxide with heptyloxy, styryl-COOH) | 10000<br>10000<br>10000 | 16<br>3<br>9 | α<br>β<br>γ | 77<br>4700<br>4200 |
| (structure 2: thiochromane S,S-dioxide with heptyloxy, trienoic acid) | 10000<br>10000<br>10000 | 9<br>14<br>16 | α<br>β<br>γ | 27<br>5100<br>2400 |
| (structure 3: benzothiepine S,S-dioxide with n-C$_6$H$_{13}$, trienoic acid) | 10000<br>10000<br>10000 | 11<br>35<br>33 | α<br>β<br>γ | 47<br>4900<br>1000 |
| (structure 4: thiochromane S,S-dioxide with n-C$_7$H$_{15}$, styryl-COOH) | 10000<br>10000<br>10000 | 16<br>15<br>32 | α<br>β<br>γ | 70<br>1900<br>2300 |
| (structure 5: thiochromane (S) with n-C$_7$H$_{15}$O, trienoic acid) | 10000<br>10000<br>10000 | 27<br>17<br>36 | α<br>β<br>γ | 200<br><10000<br><10000 |
| (structure 6: benzothiepine S,S-dioxide with n-C$_7$H$_{15}$O, trienoic acid) | 10000<br>10000<br>10000 | 12<br>20<br>30 | α<br>β<br>γ | 180<br>6400<br>2200 |
| (structure 7: benzothiepine S,S-dioxide with heptyloxy, styryl-COOH) | 10000<br>10000<br>10000 | 14<br>7<br>18 | α<br>β<br>γ | 190<br>3000<br>2500 |

-continued

| Structure | Transactivation | | RAR Binding |
|---|---|---|---|
| | EC$_{50}$ | % MAX | IC$_{50}$ |
| (structure: 4,4-dimethyl thiochromane-1,1-dioxide with O-n-heptyl and 2-naphthoic acid) | 10000<br>10000<br>10000 | 8<br>17<br>14 | α 360<br>β 2800<br>γ 1400 |
| (structure: methyl-benzothiepine sulfone with O-n-C$_7$H$_{15}$ and propenyl-benzoic acid) | 10000<br>10000<br>10000 | 5<br>7<br>14 | α 530<br>β 5100<br>γ 3000 |
| (structure: 4,4-dimethyl thiochromane-1,1-dioxide with O-CH$_2$-n-C$_6$H$_{13}$ and ethynyl-benzoic acid) | 10000<br>10000<br>10000 | 18<br>6<br>20 | α 240<br>β 3500<br>γ 2900 |
| (structure: 4,4-dimethyl thiochromane sulfoxide with O-n-C$_7$H$_{15}$ and retinoic acid chain) | 10000<br>10000<br>10000 | 13<br>10<br>11 | α 440<br>β >10000<br>γ 3700 |
| (structure: methyl-benzothiepine-1,1-dioxide with CH$_2$-n-C$_7$H$_{15}$ and propenyl-benzoic acid) | 10000<br>10000<br>10000 | 18<br>13<br>36 | α 200<br>β 3300<br>γ 1800 |
| (structure: 4,4-dimethyl thiochromane-1,1-dioxide with O-N(n-C$_7$H$_{15}$) and retinoic acid chain, COOH) | 10000<br>10000<br>10000 | 24<br>31<br>20 | α 450<br>β >10000<br>γ >10000 |

-continued

| Structure | Transactivation | | RAR Binding | |
|---|---|---|---|---|
| | $EC_{50}$ | % MAX | $IC_{50}$ | |
| (structure) | 10000 | 20 | α | 250 |
| | 10000 | 32 | β | 2500 |
| | 10000 | 46 | γ | 1300 |
| (structure) | 10000 | 8 | α | 390 |
| | 10000 | 21 | β | 6900 |
| | 10000 | 25 | γ | 2600 |
| (structure) | 10000 | 14 | α | 580 |
| | 10000 | 37 | β | 3800 |
| | 10000 | 54 | γ | 2600 |
| (structure) | 10000 | 11 | α | 160 |
| | 10000 | 22 | β | 6900 |
| | 10000 | 24 | γ | 3400 |

$EC_{50}$'s were determined relative to ATRA, with both compounds at 10000 nM. Values are expressed as a percentage of transactivation relative to ATRA.

Particularly preferred compounds within the family of compounds of Formula I include the RARα selective antagonists of Formula Ia and Ib:

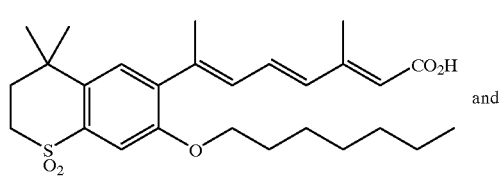

Formula Ia and

Formula Ib

In another aspect, RAR antagonists which can be used in this invention have the structures of Formula II and III:

Formula II

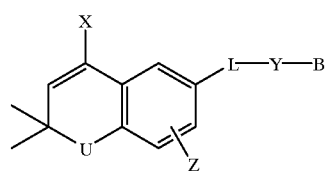

Formula III wherein:

X is aryl or heteroaryl, both optionally substituted independently with alkyl or halo;

L is C(=G)NH or NH(C=G), where G is oxygen or sulfur;

Y is phenylene, naphthylene or heteroarylene, all optionally substituted with alkyl or halo;

B is carboxyl or loweralkoxycarbonyl;

Z is alkyl, halo, $NO_2$ or OH; and

U is oxygen or sulfur.

Preferred compounds within the family of compounds of Formulas II and III include the RARα selective antagonists of Formula Ia and IIIa:

Formula IIa

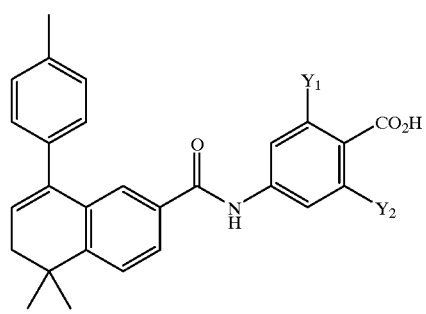

Formula IIIa

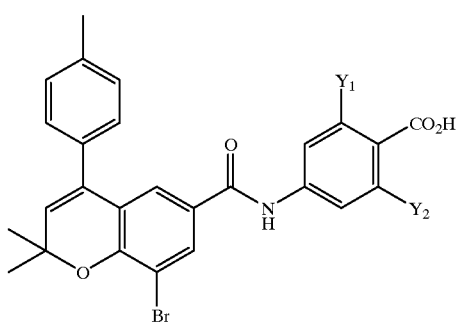

wherein $Y_1$ and $Y_2$ are independently hydrogen or halo (preferably fluoro). Particularly preferred are the compounds of Formula IIIa where $Y_1$ is fluoro and $Y_2$ is hydrogen, and $Y_1$ is fluoro and $Y_2$ is fluoro.

A related RAR antagonist that may be used in this invention is the compound of Formula IV.

Formula IV

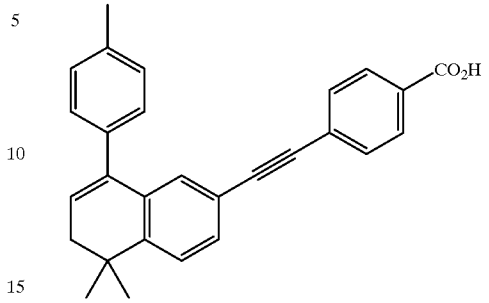

In another aspect, RAR antagonists which can be used in this invention are of Formula V:

Formula V

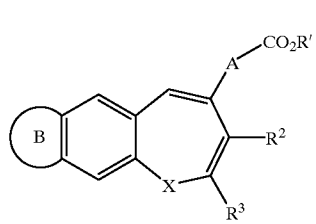

wherein:

B is a fused 5, 6 or 7 membered carbocyclic ring, optionally alkyl or halo substituted;

X is $NR^4$, O, S, or $CHR^4$ (where $R^4$ is H or alkyl);

A is phenylene or pyridinediyl;

$R^1$ is H or alkyl;

$R^2$ and $R^3$ are independently H or alkyl, or $R^2$ and $R^3$ together form a phenyl, naphthyl, tetrahydronaphthyl or cycloalkyl ring.

Preferred compounds within the family of compounds of Formula V include the RARα selective antagonists of Formula Va and Vb:

Formula Va

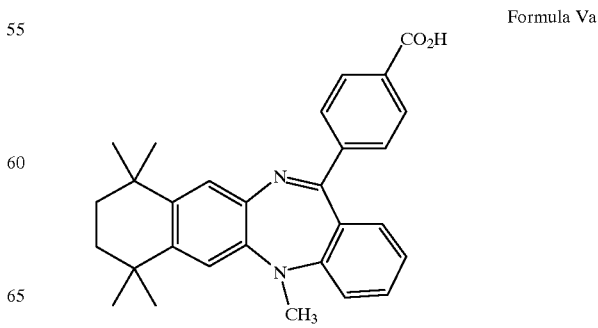

-continued

Formula Vb

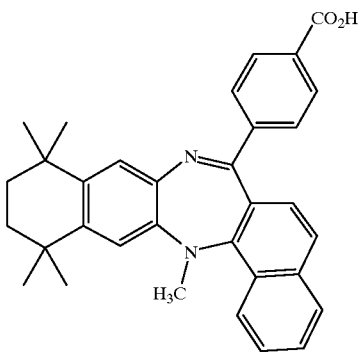

In another aspect, RAR antagonists which can be used in this invention have the structure of Formula VI:

Formula VI

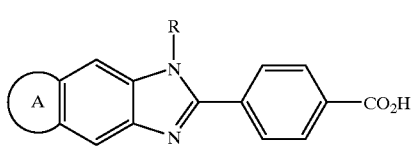

wherein:
A is a fused 5, 6, or 7 membered carbocyclic ring, optionally alkyl substituted; and
R is $C_{3-10}$ alkyl, cycloalkyl, aryl or aralkyl.

Preferred compounds within the family of compounds of Formula VI include the RARα selective antagonists of Formula VIa where R is phenyl or benzyl.

Formula VIa

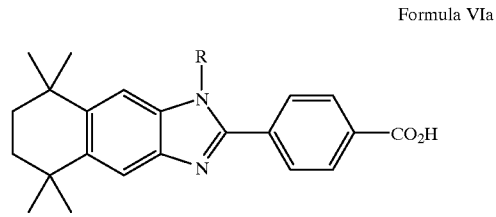

A nonselective RAR antagonist that may be used in this invention is a compound of Formual VIIa.

Formula VIIa

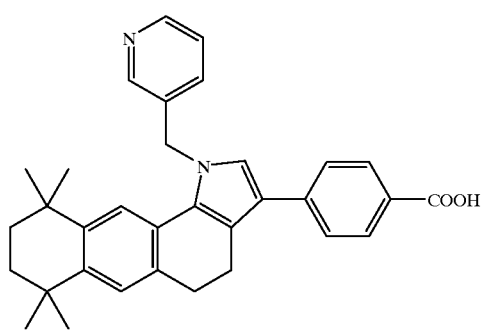

The compounds are generally made by methods known to one of skill in the art. They can be made by methods described in the above-cited references, all incorporated by reference herein.

Utility and Administration

The methods of treatment disclosed herein may be used for reducing mucous secretions, particularly in the airway. Treatment with RAR antagonists, particularly, RARα selective antagonists, is useful to suppress overexpression of mucin associated with lung inflammation and to suppress mucous hypersecretion associated with general epithelial cell inflammation. As such, the methods disclosed herein are useful for treating diseases such as asthma, emphysema, chronic obstructive pulmonary disease, bronchitis, bronchiectasis, cystic fibrosis, postoperative atelectasis, and the like.

The particular dosage of a RAR antagonist or an RARα selective antagonist required to reduce mucin hypersecretion according to this invention will depend on the severity of the condition, the route of administration and related factors which will be decided by the attendant physician. Typically, the dosage will range between about 0.2 and 20 mg/kg body weight per day, preferably from about 0.5 to about 15 mg/kg body weight per day, most preferably from about 1 to 2.5 mg/kg. For a 50 kg human subject, the daily dose of active ingredient is from about 25 to 750 mgs, preferably from about 50 to about 125 mgs. This dosage may be delivered in a conventional pharmaceutical composition by a single administration, by multiple applications, or via controlled release, as needed to achieve the most effective results. Dosing will continue for as long as is medically indicated, which depending on the severity of the disease may range from a few weeks to several months.

Typically, a pharmaceutically acceptable composition, such as a salt, or prodrug of the the RAR antagonist in a pharmaceutically acceptable carrier or diluent is administered. In the context of the present invention, pharmaceutically acceptable salts include any chemically suitable salt known in the art of retinoid antagonists as applicable for administration to human patients. Examples of conventional salts known in the art include the alkali metal salts such as sodium and potassium salts, the alkaline earth metal salts such as calcium and magnesium salts, and ammonium and alkyl ammonium salts. Particularly preferred prodrug compositions of the RAR antagonists include hydrolyzable ester derivatives such as aromatic and benzyl esters, or lower alkyl esters e.g., ethyl, t-butyl, cyclopentyl and the like.

Representative delivery regimens include oral, parenteral (including subcutaneous, intramuscular and intravenous), rectal, buccal (including sublingual), transdermal, pulmonary and intranasal. One method of pulmonary administration involves aerosolization of an aqueous solution of an RAR antagonist. Aerosolized compositions may include the compound packaged in reverse micelles or liposomes. Typical pulmonary and respiratory delivery systems are described in U.S. Pat. Nos. 5,607,915, 5,238,683, 5,292,499, and 5,364,615 and WO 97/39745. Localized delivery such as pulmonary delivery typically employs dosages 5–10 fold lower than systemic delivery.

A preferred aerosolized formulation is prepared by solubilizing the retinoid antagonist in a chlorofluorocarbon solvent in the presence of an alkylamine as described in WO 97/39745. Typical chlorofluorocarbons include HCFC-123, HCFC-134A or HCFC-227. Preferred alkylamines include secondary, tertiary and quaternary alkylamines having $C_{2-8}$ alkyl groups, e.g., trioctylamine, spermine, tetramethylammonium bromide and the like. Aerosolized formulations may be advantageously delivered directly to the epithelial cells of the respiratory tract using metered dosage inhalers.

Other formulations which may be used to deliver the retinoid antagonists for treatment of mucin secretion use a dry powder carrier as described in U.S. Pat. No. 5,376,386 by coating the retinoid onto the surface of the carrier in a micronizer.

The treatment methods of this invention also include systemic administration of RAR antagonists in simultaneous or sequential combination with a further active ingredient for improving mucociliary clearance of airway mucus or reducing mucous viscosity. Representative active ingredients for improving mucociliary clearance include, for example, sodium channel blockers (e.g. amiloride) or lantibiotics (e.g. duramycin, nisin or subtilin). Representative active ingredients for reducing mucous viscosity include N-acetylcysteine, homocysteine and phospholipids.

RAR antagonists will typically be administered as pharmaceutical compositions in admixture with a pharmaceutically acceptable, non-toxic carrier. As mentioned above, such compositions may be prepared for parenteral (subcutaneous, intramuscular or intravenous) administration, particularly in the form of liquid solutions or suspensions; for oral or buccal administration, particularly in the form of tablets or capsules; for intranasal administration, particularly in the form of powders, nasal drops or aerosols; and for rectal or transdermal administration. Any conventional carrier material can be employed. The carrier material can be any organic or inorganic carrier material, such as water, gelatin, gum arabic, lactose, starch, magnesium stearate, talc, polyalkylene glycols, petroleum jelly and the like.

Liquid formulations for parenteral administration may contain as excipients sterile water or saline, alkylene glycols such as propylene glycol, polyalkylene glycols such as polyethylene glycol, oils of vegetable origin, hydrogenated naphthalenes and the like. They may employ slightly acidic buffers in pH ranges of about 4 to about 6. Suitable buffers include acetate, ascorbate and citrate at concentrations ranging from about 5 mM to about 50 mM. For oral administration, the formulation can be enhanced by the addition of bile salts or acylcamitines.

Formulations for nasal administration may be solid and may contain excipients, for example, lactose or dextran, or may be aqueous or oily solutions for use in the form of nasal drops or metered spray. Particular nasal formulations include dry powders suitable for conventional dry powder inhalers (DPI's), liquid solutions or suspensions suitable for nebulization and propellant formulations suitable for use in metered dose inhalers (MDI's). For buccal administration typical excipients include sugars, calcium stearate, magnesium stearate, pregelatinated starch, and the like.

When formulated for nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Solid forms for oral administration include tablets, hard and soft gelatin capsules. pills, sachets, powders, granules and the like. Each tablet, pill or sachet may contain from about 0.5 to about 20 mg of RAR antagonist, preferably from about 2 to about 10 mg. Preferred solid oral dosage forms include tablets, two-piece hard shell capsules and soft elastic gelatin (SEG) capsules. SEG capsules are of particular interest because they provide distinct advantages over the other two forms (see Seager, H., "Soft gelatin capsules: a solution to many tableting problems"; *Pharmaceutical Technology*, 9, (1985). Some of the advantages of using SEG capsules are: a) dose-content uniformity is optimized in SEG capsules because the drug is dissolved or dispersed in a liquid that can be dosed into the capsules accurately b) drugs formulated as SEG capsules show good bioavailability because the drug is dissolved, solubilized or dispersed in an aqueous-miscible or oily liquid and therefore when released in the body the solutions dissolve or are emulsified to produce drug dispersions of high surface area and c) degradation of drugs that are sensitive to oxidation during long-term storage is prevented because the dry shell.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

The following are representative pharmaceutical formulations for using RAR antagonists as described herein for inhibition of mucin secretion.

Tablet formulation
The following ingredients are mixed intimately and pressed into single scored tablets.

| Ingredient | Quantity per tablet, mg |
| --- | --- |
| RAR antagonist | 20 |
| cornstarch | 5 |
| croscarmellose sodium | 2.5 |
| lactose | 12 |
| magnesium stearate | 0.5 |

Capsule formulation
The following ingredients are mixed intimately and loaded into a hard-shell gelatin capsule.

| Ingredient | Quantity per capsule, mg |
| --- | --- |
| RAR antagonist | 20 |
| lactose, spray-dried | 15 |
| magnesium stearate | 0.2 |

Suspension formulation
The following ingredients are mixed to form a suspension for or administration.

| Ingredient | Amount |
| --- | --- |
| RAR antagonist | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable formulation
The following ingredients are mixed to form an injectable formulation.

| Ingredient. | Amount |
| --- | --- |
| RAR antagonist | 0.2 g |
| sodium acetate buffer solution, 0.4 M | 2.0 ml |

-continued

Injectable formulation
The following ingredients are mixed to form an injectable formulation.

| Ingredient. | Amount |
| --- | --- |
| HCl (1N) or NaOH (1N) | q.s. to suitable pH |
| water (distilled, sterile) | q.s. to 20 ml |

Nasal formulation
The following ingredients are mixed to form a suspension for nasal administration.

| Ingredient | Amount |
| --- | --- |
| RAR antagonist | 20 mg/ml |
| citric acid | 0.2 mg/ml |
| sodium citrate | 2.6 mg/ml |
| benzalkonium chloride | 0.2 mg/ml |
| sorbitol | 35 mg/ml |
| sodium taurocholate or glycocholate | 10 mg/ml |

The following preparations and examples are given to enable those skilled in the art to more clearly understand and to practice the present invention. They should not be considered as limiting the scope of the invention, but merely as being illustrative and representative thereof.

The following RAR agonists and antagonists are used in the following Examples.

Compound X: RARα sleective agonist

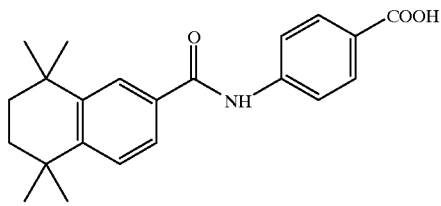

4-(5,6,7,8-tetrahydro-5,5,8,8-dimethyl-6 naphthalenyl carboxamido)benzoic acid).

Compound Y: RARβ selective agonist

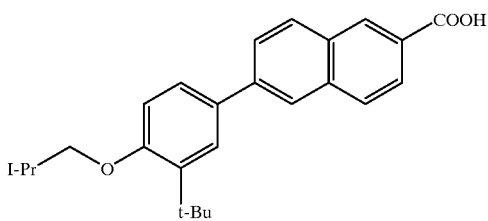

Compound CD 437: RARγ selective agonist, (6-[3-(1-adamantyl)-4-hydroxyphenyl]-2-naphthalenecarboxylic acid); see, Martin, B., Bernardon, J. M., Cavey, M. T., Bernard, B., Carlavan, I., Charpentier, B., Pilgrim, W. R., Shroot, B., and Reichert, U. (1992) *Skin Pharmacol* 5(1:57–65; Charpentier, B., Bernardon, J. M., Eustache, J., Millois, C., Martin, B., Michel, S., and Shroot, B. (1995) *J-Med-Chem* 38(26):4993–5006.

SRI 11217: RXR agonist, (4-[1-(5,6,7,8-tetrahydro-5,5,8,8,-tetramethyl-2-naphthalenyl)-2-methylpropenyl]-benzoic acid) see, Fanjul, A., Dawson, M. I., Hobbs, P. D., Jong, L., Cameron, J. F., Harlev, E., Graupner, G., Lu, X. P., and Pfahl, M. (1994) *Nature* 372(6501):107–11

SRI 11302: Anti-AP-1 retinoid, ((E)-3-methyl-9-(2,6,6-trimethylcyclohexenyl)-7-(4-methyl-phenyl)-2,4,6,8-nonatetraenoic acid) see Fanjul, A., Dawson, M. I., Hobbs, P. D., Jong, L., Cameron, J. F., Harlev, E., Graupner, G., Lu, X. P., and Pfahl, M. (1994) *Nature* 372(6501):107–11; and Mills, K. J., Vollberg, T. M., Nervi, C., Grippo, J. F., Dawson, M. I., and Jetten, A. M. (1996) *Cell Growth Differ.* 7(3): 327–337.

Compound Z: (RARα selective antagonist), (p-[(E)-2-[3'4'-Dihydro-4,4'-dimethyl-7'-(heptyloxy)-2'H-1-benzothiopyran-6'-yl]propenyl]benzoic acid 1'1'-dioxide (Compound Ia)

EXAMPLE 1

RAR Transactivation of Steady State Mucin Genes

Transactivation of mucin genes in normal primary human bronchial epithelial cells (NHBE) was performed as described by Gray et al. *Am. J. Respir. Biol.*, 14:104–112 (1996). Primary human airway epithelial cells were cultured on porous Transwell membranes (Corning/Costar) in defined media in the absence of all-trans retinoic acid (ATRA) for 7 days. After seven days, fresh media±ATRA or selective retinoid, was added to the basal culture compartment to create an air-liquid interface (ALI). ATRA and/or selective retinoids were used at a concentration or $1 \times 10^{-7}$ M. The selective retinoids used were: Compound X (RARα selective agonist), RXR agonist (SRI 11217) and anti-AP1 retinoid (SRI 11302). After seven additional days of culture the media was harvested for analysis of secreted mucin gene product using specific ELISA as previously described (Gray et al). The cell layer was lysed using a guanidinium-based buffer (TRIZOL/Sigma) for RNA extraction and analysis. Amplification of MUC2 and MUC5AC RNA was performed by standard RT-PCR using appropriate selective primer and mimics pairs (Guzman et al., *Am. J. Physiol.* 271 (*Lung Cell Mol Physiol*.15): L1023–L1028 (1996) and PCR products were detected in ethedium bromide stained agarose gels.

Data represent samples run in triplicate and pooled for RNA analysis. Results are shown in FIG. 1(*a*). Both ATRA and an RARα selective agonist (Compound X) induce both MUC2 and MUC5AC gene induction. RXR selective-agonist, SRI 11217, had no effect on induction of either gene.

Corresponding mucin protein secretion data are shown in FIG. 1(*b*) as ELISA data representing results from separate samples run in triplicate. Data presented as mean±sem. The mucin protein secretion data were consistent with gene induction results.

EXAMPLE 2

Concentration Dependent Inductuction of Steady State Mucin Genes using RAR-Selective Retinoids Transactivation of mucin genes in NHBE was performed as described above with the exception that media was supplemented with RAR alpha (RARα), beta (RARβ), or gamma (RARγ)-selective retinoids on days 7 through day 14. The RAR alpha (RARα), beta (RARβ), or gamma (RARγ)-selective retinoids were compounds X, Y and CD-437 respectively. Compounds were dosed at a concentration range of $1 \times 10^{-9}$ M to $1_{33\ 10}^{-6}$ M. As shown in FIG. 2, the RARα selective agonist was the most potent inducer of MUC2 and MUC5AC gene activation as demonstrated by transactivation activity at $1 \times 10^{-9}$ M. Induction of MUC2 and MUC5AC by RARα or RARγ selective agonists was minimal even at the highest dose of compound ($1 \times 10^{-6}$ M).

EXAMPLE 3

RA-Induced Mucin Gene Expression is Inhibited by RARα-Selective Antagonist

Transactivation of mucin genes in NHBE was performed as described above. On days 7 through day 14 cells were cultured with 1×10⁻⁶ M RARα antagonist, Compound Z, alone or in combination with 1×10⁻⁷ M ATRA or RARα selective agonist, Compound X. The effects on mucin gene transactivation and expression were determined by RT-PCR and ELISA as described above. RARα selective antagonist, Compound Z, had no effect on MUC2 or MUC5AC gene expression. ATRA and RARα selective agonist, Compound X were potent inducers of MUC2 or MUC5AC. However this effect was completely inhibited by co-treatment with Compound Z. The inhibition was observed both at the level of RNA transcription (FIG. 3a) and mucin protein secretion (FIG. 3b)

EXAMPLE 4

ATRA Enhances LPS-Induced Goblet Cell Hyperplasia and Mucus Hypersecretion in Rats All-trans retinoic acid (ATRA) was evaluated for its effects on mucous hypersecretion in the rat model of endotoxin/lipopolysacharide (LPS)-induced lung inflammation (Steiger et al. *J. Am. Respir. Cell Mol. Biol.*, 12:307–314 (1995)). Animals were divided into treatment groups of approximately six. Lung inflammation was induced in male Long Evans rats by repeated instillation of LPS (LPS derived from *Pseudomonas aeriginos*; Sigma Chemical) 400 μg/Kg/dose/day for three days. ATRA was dissolved in DMSO (20 mg/ml) and stored at −20 C. Fresh working stocks were prepared fresh daily by dilution in PBS to a final concentration of 2 mg/ml. Animals treated with ATRA (2 mg/kg ip) were dosed once daily by intraperitoneal injection, starting 24 hours prior to the first LPS challenge. Two control groups were included in the study, treatment with vehicle (DMSO/PBS) followed by LPS and treatment with ATRA alone. Animals were sacrificed 24 hours after the last LPS challenge by exsanguination under deep anesthesia.

The lungs were lavaged with phosphate buffered saline (2×5 ml) to wash out mucous layer. The lavage fluid (BAL) was centrifuged for 10 min at 500×g and the cell-free supernate was frozen and stored −20° C. until analyzed for secreted mucin by Alcian-blue/PAS dot blot assay to determine relative contribution of neutral and acidic mucins. Standard curves were generated using bovine intestinal mucins (Sigma) TYPE 1 (Alc. blue/acidic mucins) and TYPE II (PAS+/neutral mucin). Each sample was assayed in triplicate and data presented as gg/ml total mucin. (FIG. 4b)

After lavage the lungs were perfused with 10% neutral buffered formalin by intratracheal instillation at a constant rate (5 ml at 1 ml/min). The left lobe was excised and immersed in fixative for 24 hours prior to processing. Standard methods were used to prepare 5 μm paraffin sections. Sections were stained with Alcian blue (pH 2.5) and periodic acid/Schiffs reagent to detect mucosubstances within the lung tissue. Morphometric analysis for goblet hyperplasia was performed by counting all airways ≧2 mm in diameter and determining the percentage of airways that contain Alc/PAS positive cells (FIG. 4a).

EXAMPLE 5

Effects of ATRA and RARα Selective Antagonist on LPS-Induced Mucin Gene Expression In Vitro An in vitro assay was established to screen retinoid-based compounds for their effects on LPS-induced mucin gene expression using a continuous human lung epithelial cell line, NIH-292. NIH-292 cells were cultured in standard T-75 tissue culture flasks in DMEM/F12 media containing 10% fetal bovine serum (FBS). Upon confluence the media was changed to defined medium Optimem (Sigma) supplemented with 1% FBS 24 hours prior to challenge with 10 μg/ml LPS (*P. aeriginos*, Sigma Chemical). RAR selective antagonist, Compound Z, was added 24 hours prior to LPS challenge. ATRA and specific retinoids were prepared as DMSO stocks. Cells were harvested 6 or 24 hours after LPS challenge using a guanidinium-based buffer (TRIZOL/Sigma) for RNA extraction and analysis. Amplification of β-actin, MUC1, MUC2 and MUC5AC specific RNA was performed by using an automated fluorescent detection method for quantitation of real time RT-PCR (TAQMAN, Applied Biosystems/Perkin Elmer). Standard curves were generated for each of the relevant mucin RNAs using control plasmid. Analysis was performed in triplicate from duplicate samples. Results are shown in FIG. 5 expressed in pg/ml and show that RARα selective antagonists inhibit LPS induced mucin gene expression.

A dose response experiment with different concentrations of Compound Z (Ia) is shown in FIG. 7. Cells were stimulated with LPS in the presence or absence of Ia. MUC5AC specific mRNA was measured and is graphed normalized relative to glyceraldehyde phosphate 3-dehydrogenase control. The results show that Ia is a potent inhibitor of MUC5AC gene transcription with an IC50<10 nM.

EXAMPLE 6

RARα Selective Antagonists Inhibit Mucin Hypersecretion in Mice and Rats

The effect of RARα selective antagonists Ia and Ib on mucous hypersecretion in the rat and mouse models of LPS-induced lung inflammation was evaluated according to the procedure of Example 4. Animals were treated with compound (10 mg/kg) or vehicle daily starting 72 hours prior to LPS challenge. The results are shown in FIG. 6 and show that both these RAR α selective antagonists reduced the amount of mucous hypersecretion relative to vehicle.

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined with reference to the following appended claims, along with the full scope of equivalents to which such claims are entitled.

The patents, patent applications and publications cited in this application are hereby incorporated by reference in their entirety for all purposes to the same extent as if each individual patent, patent application or publication were so individually denoted.

What is claimed is:

1. A method of inhibiting mucin production in a mammal comprising administering to the mammal an RAR antagonist, or prodrug or pharmaceutically acceptable salt thereof.

2. The method of claim 1, wherein the RAR antagonist is an RARα selective antagonist.

3. The method of claim 2, wherein the RARα selective antagonist binds to the RARα receptor with an $IC_{50}$ of about 10000 nM or less.

4. The method of claim 2, wherein the selectivity of the RARα selective antagonist for the RARα receptor at least about 2:1 relative to the RARβ and RARγ receptors.

5. The method of claim 1, wherein the RAR antagonist is selected from compounds of Formula I:

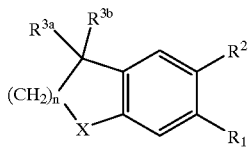

Formula I wherein:

X is S, SO, or $SO_2$;

$R^1$ is $C_{7-10}$ alkyl or $C_{7-10}$ alkoxy;

$R^2$ is carboxyaryl, loweralkoxycarbonylaryl, carboxyalkenyl, lowealkoxycarbonylalkenyl, carboxyalkynyl, loweralkoxycarbonylalkynyl, carboxyarylalkenyl, loweralkoxycarbonylarylalkenyl, carboxyarylalkynyl or loweralkoxycarbonylarylalkynyl;

$R^{3a}$ and $R^{3b}$ are independently hydrogen or $C_{1-4}$ alkyl; and n is an integer from 1 to 3 inclusive.

6. The method of claim 5, wherein:
X is $SO_2$; and
n is 2.

7. The method of claim 6, wherein:
$R^1$ is heptyloxy and
$R^2$ is:

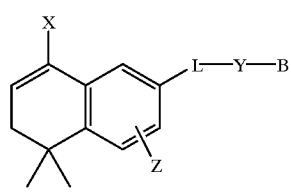

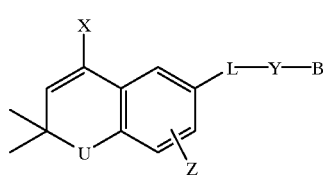

where $R^4$ is carboxy.

8. The method of claim 1, wherein the RAR antagonist is selected from compounds of the Formula II and Formula III.

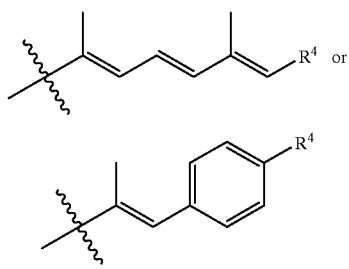

Formula II

Formula III wherein:

X is aryl or heteroaryl;

L is C(=G)NH or NH(C=G), where G is oxygen or sulfur;

Y is aryl or heteroaryl;

B is carboxy or loweralkoxycarbonyl;

Z is alkyl, halo, $NO_2$ or OH; and

U is oxygen or sulfur.

9. The method of claim 1, wherein the wherein the RAR antagonist is selected from compounds of Formula V:

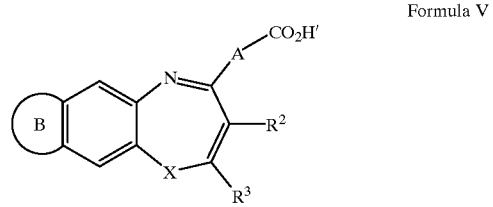

Formula V wherein:

B is a fused 5, 6 or 7 membered carbocyclic ring;

X is $NR^4$, O, S, or $CHR^4$ (where $R^4$ is H or alkyl);

A is phenylene or pyridinediyl;

$R^1$ is H or alkyl;

$R^2$ and $R^3$ are independently H or alkyl, or $R^2$ and $R^3$ together form a phenyl, naphthyl, tetrahydronaphthyl or cycloalkyl ring.

10. A method of treating a disease associated with mucin hypersecretion in a mammal comprising administering to the mammal an RAR antagonist, or prodrug or pharmaceutically acceptable salt thereof.

11. The method of claim 10, wherein the RAR antagonist is an RARα selective antagonist.

12. The method of claim 11, wherein the RARα selective antagonist binds to the RARα receptor with an $IC_{50}$ of about 10000 nM or less.

13. The method of claim 11, wherein the selectivity of the RARα selective antagonist for the RARα receptor at least about 2:1 relative to the RARβ and RARγ receptors.

14. The method of claim 10, wherein the RARα antagonist is selected from compounds of the Formula I:

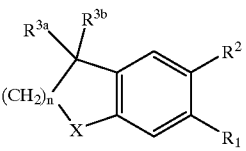

Formula I wherein:

X is S, SO, or $SO_2$;

$R^1$ is $C_{7-10}$ alkyl or $C_{7-10}$ alkoxy;

$R^2$ is carboxyaryl, loweralkoxycarbonylaryl, carboxyalkenyl, lowealkoxycarbonylalkenyl, carboxyalkynyl, loweralkoxycarbonylalkynyl, carboxyarylalkenyl, loweralkoxycarbonylarylalkenyl, carboxyarylalkynyl or loweralkoxycarbonylarylalkynyl;

$R^{3a}$ and $R^{3b}$ are independently hydrogen or $C_{1-4}$ alkyl; and n is an integer from 1 to 3 inclusive.

15. The method of claim 14, wherein:
X is $SO_2$; and
n is 2.

16. The method of claim 15, wherein:
R¹ is heptyloxy and
R² is:

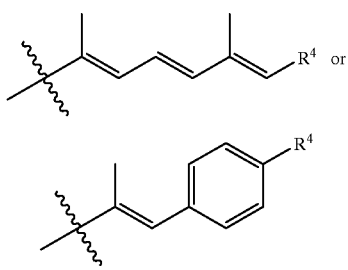

where R⁴ is carboxy.

17. The method of claim 10, 11 or 14, wherein the disease is chronic obstructive pulmonary disease or asthma.

18. A method of inhibiting mucin gene expression in a human epithelial cell by contacting the cell with an RAR antagonist, or prodrug or pharmaceutically acceptable salt thereof.

19. The method of claim 18, wherein the RAR antagonist is an RARα selective antagonist.

20. The method of claim 19, wherein the RAR antagonist is is selected from compounds of the Formula I:

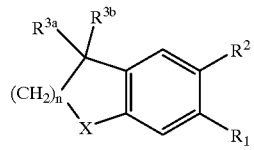

Formula I wherein:

X is S, SO, or SO₂;

R¹ is $C_{7-10}$ alkyl or $C_{7-10}$ alkoxy;

R² is carboxyaryl, loweralkoxycarbonylaryl, carboxyalkenyl, lowealkoxycarbonylalkenyl, carboxyalkynyl, loweralkoxycarbonylalkynyl, carboxyarylalkenyl, loweralkoxycarbonylarylalkenyl, carboxyarylalkynyl or loweralkoxycarbonylarylalkynyl;

$R^{3a}$ and $R^{3b}$ are independently hydrogen or $C_{1-4}$ alkyl; and n is an integer from 1 to 3 inclusive.

21. The method of claim 20, wherein:
X is SO₂; and
n is 2.

22. The method of claim 21, wherein:
R¹ is heptyloxy and
R² is:

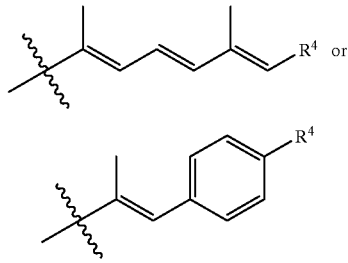

where R⁴ is carboxy.

* * * * *